United States Patent [19]

Francon et al.

[11] Patent Number: 5,075,110

[45] Date of Patent: Dec. 24, 1991

[54] STABILIZING VACCINES

[75] Inventors: Alain J. Francon, Bessenay; Bernard J. Montagnon, L'Arbresle, both of France

[73] Assignee: Institut Merieux, Lyons, France

[21] Appl. No.: 369,144

[22] Filed: Jun. 21, 1989

[30] Foreign Application Priority Data

Jun. 30, 1988 [FR] France ................. 88 08806

[51] Int. Cl.$^5$ .............. A61K 39/12; A61K 37/00; A61K 31/17
[52] U.S. Cl. ........................ 424/89; 424/93; 514/580; 514/588; 514/970
[58] Field of Search .............. 514/580, 588, 970; 424/89, 93

[56] References Cited

U.S. PATENT DOCUMENTS 4,333,922 6/1982 Herschler ...................... 424/89
4,851,391 7/1989 Hempel et al. ................ 514/588

Primary Examiner—Frederick E. Waddell
Assistant Examiner—Kevin Weddington
Attorney, Agent, or Firm—Larson and Taylor

[57] ABSTRACT

A process for stabilizing attenuated lyophilized vaccines with a compound having the general formula:

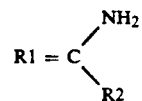

wherein R1 is an oxygen atom or a sulphur atom and R2 is a NH$_2$ group or a linear chain, unsaturated or not, selected from the group consisting of —O—C . . . , —NH—C . . . , and —C . . . .

10 Claims, No Drawings

STABILIZING VACCINES

This invention relates to a process for stabilizing vaccines and associated attenuated virus vaccines which are kept in lyophilized form with at least a lyophilization excipient.

The invention also relates to compositions obtained with the inventive process.

A number of vaccines against viral diseases are made from attenuated live viruses. Lyophilization is used for their preservation. This dessication technique for previously frozen products can be applied to vaccines which are made from suitable mixtures of attenuated viruses with lyophilizing excipients whose function is to protect the product (STONES P. B., WARDEN D. and KERR J., Symposium on stability and effectiveness of measles, poliomyelitis and pertussis vaccines (1976), Zagreb—Yugoslavia. The stability of measles vaccine and factors affecting its efficacy). With associated vaccines, each valence generally has its own lyophilization excipient.

A notable loss of lyophilized vaccine activity can however be detected with some vaccines in spite of their lyophilization when they are kept at room temperatures. This loss of activity is believed to be partly due to a degradation of attenuated viral particles with some attenuated viruses being more liable than others to this phenomenon.

An object of this invention is to obviate this problem by providing a stabilizing process leading to a better preservation with time of vaccines and associated vaccines comprising attenuated viruses which are kept in lyophilized form.

An object of this invention is to provide a process which is simple to carry out, safe and inexpensive, using products that are available in sufficient quantity and free from toxicity towards humans.

Another object of this invention is, a process for stabilizing vaccines and associated vaccines comprising attenuated viruses which are kept in lyophilized form in the presence of at least one lyophilization excipient, characterized in that a suitable amount of at least one compound of the general formula:

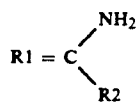

wherein R1 is an oxygen atom or a sulphur atom and R2 is a $NH_2$ group or a linear chain, unsaturated or not, of type: —O—C..., —NH—C... or —C..., possibly hydroxylsubstituted, is added, preferably before lyophilization.

It is therefore possible to consider components having formula:

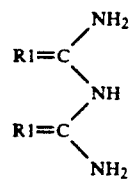

for instance biuret.

The stabilizing compound according to the invention does not take the place of customary lyophilization excipients, but adds to the stabilization of vaccines and associated vaccines intended by the invention.

Preferably the stabilizing component is urea which is interestingly a physiological compound naturally found in the body:

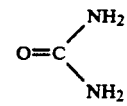

Among the other stabilizing compounds according to the invention

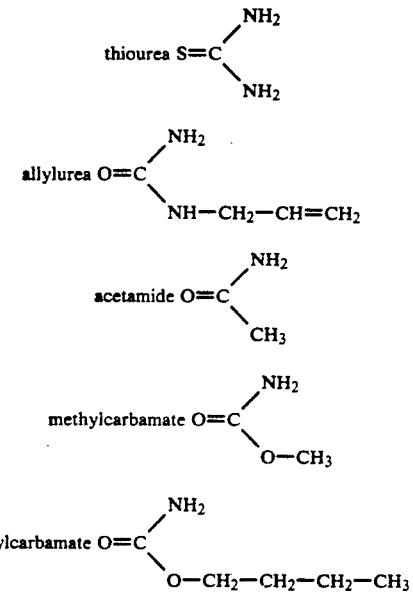

can be mentioned.

This list is naturally not limiting. The stabilizing compound is used at a very small final concentration, for instance about 0.5% (weight). Each compound can have a concentration varying within a wide or narrow interval, with a stabilizing effect, and a negative effect towards the virus(es) beyond that interval. For instance with allylurea this interval is preferably not greater than 0.5%.

Urea can be used at a final concentration between about 0.125 and 2%, it being understood that this preferred concentration interval is not limiting.

The stabilizing compound is preferably introduced before lyophilization. The effect of the stabilizing compound can however be demonstrated even if it is introduced subsequently (rehydration and second lyophilization).

The following detailed study illustrates the triple measles, mumps and rubella vaccine wherein the measles and mumps valences are liable to important losses of activity. But the invention relates to all attenuated virus vaccines which are difficult to preserve in the lyophilized state for similar reasons, such as the presence of neuraminidase and/or sensitive glycoproteins.

The results of a study of the effect of urea on several batches of commercial vaccines are collected in Table I.

TABLE I

Comparison of infective title losses after 7 days at +37° C., with commercial batches, with and without urea.

| VALENCE | UREA % | | TITLES IN CCID 50/DOSE | | Average loss (log)* |
|---|---|---|---|---|---|
| | | | −20° C. | 7 days at +37° C. | |
| MEASLES | 0 | A 1264 | 3.93 | 2.73 | 0.86 |
| | | A 1265 | 3.86 | 2.97 | |
| | | A 1266 | 4.03 | 3.53 | |
| | 0.5 | B 1193 | 3.68 | 3.00 | 0.61 |
| | | B 1331 | 4.13 | 3.53 | |
| | | B 1379 | 3.98 | 3.43 | |
| MUMPS | 0 | A 1264 | 4.45 | 3.23 | 1.34 |
| | | A 1265 | 4.40 | 3.00 | |
| | | A 1266 | 4.48 | 3.07 | |
| | 0.5 | B 1193 | 4.36 | 3.80 | 0.55 |
| | | B 1331 | 4.37 | 3.80 | |
| | | B 1379 | 4.59 | 4.07 | |
| RUBELLA | 0 | A 1264 | 3.58 | 3.13 | 0.38 |
| | | A 1265 | 3.72 | 3.30 | |
| | | A 1266 | 3.57 | 3.30 | |
| | 0.5 | B 1193 | 3.49 | 3.20 | 0.34 |
| | | B 1331 | 3.43 | 3.17 | |
| | | B 1379 | 3.68 | 3.20 | |

*Decimal logarithm

For each valence of the triple vaccine one obtains a greater stability than that which is obtained with the same lyophilization excipients only but without urea added, especially after degradation for one week at 37° C., except for the rubella valence whose stability is already satisfactorily assured.

The invention will now be described in greater detail with the help of non limiting examples applying to the triple measles, mumps and rubella vaccine.

The process is identical for all these examples:

The measles, mumps and rubella concentrated viral products, which are kept frozen at low temperature, are defrozen and thereafter extemporaneously mixed. This mixture is then divided between the several tests, the lyophilizing excipient having the inventive stabilizing compound added or not. One proceeds therefore so as to obtain the following final solution proportions: measles: 1.5 volume; mumps: 0.01 volume; rubella: 1.0 volume and excipient 2.5 volumes.

These different proportions, as indicated with reference to the examples, may vary according to the concentrated viral products title and are not limiting.

The tests are divided between several small vials, then lyophilized according to a standard cycle. The stability tests are made by keeping vials during 7 days at +37° C. or during 6 days at +45° C., with controls at +4° C. These vials are then rehydrated and titrated. Activity is determined by the number of 50% infective doses in a tissue culture (DIC C50). For the limiting dilutions process, on microplates, this corresponds to the calculated theoretical dilution for which one half of cultured cupulae exhibits a characteristic cytopathological effect.

The cells used for titration of the measles and mumps valences are Vero cells and, for the rubella valence, RK13 cells. For each value indicated in the Tables, the title number is an average of at least four different titrations.

EXAMPLE 1

Effect of urea on the measles, mumps, rubella vaccine in the presence of various lyophilization excipients The various lyophilization excipients used have a customary lyophilization composition (fillers, cryoprotectors, &c). Their compositions differ as to sugars and amino acids, which is enough to alter the several valences' stability in the absence of a stabilizing compound.

The several titrations of this example were made by way of tests. A common control (T) enables one to compare the several obtained values. Activity losses after 7 days at +37° C. or after 6 days at +45° C. enable to assess the stability of each valence according to the lyophilization excipient used, as well as the stabilizing effect of urea for each of them.

TABLES A

| STABILIZER | TITLES IN CCID 50/DOSE | | | | |
|---|---|---|---|---|---|
| | 7 days at 4° C. | 7 days at +37° C. | Loss (log) | 6 days at +45° C. | Loss (log) |
| MEASLES Valence | | | | | |
| 48-3 (T) | 4.05 | 3.52 | 0.53 | 3.20 | 0.85 |
| 48-3 + U | 4.11 | 3.75 | 0.36 | 3.33 | 0.78 |
| 48-3 (T) | 4.31 | 3.57 | 0.74 | 3.08 | 1.23 |
| 16-3 | 4.20 | 3.20 | 1.00 | 3.05 | 1.15 |
| 16-3 + U | 4.40 | 3.85 | 0.55 | 3.68 | 0.72 |
| 48-3 (T) | 4.07 | 3.35 | 0.72 | 2.91 | 1.16 |
| 17-1 | 3.45 | 2.95 | 0.50 | 2.70 | 0.75 |
| 17-1 + U | 4.35 | 4.05 | 0.30 | 3.60 | 0.75 |
| MUMPS Valence: | | | | | |
| 48-3 (T) | 4.03 | 3.04 | 0.99 | 2.86 | 1.17 |
| 48-3 + U | 4.28 | 3.99 | 0.29 | 3.47 | 0.81 |
| 48-3 (T) | 4.28 | 3.37 | 0.91 | 3.07 | 1.21 |
| 16-3 | 4.65 | 3.70 | 0.95 | 3.30 | 1.35 |
| 16-3 + U | 4.58 | 4.00 | 0.58 | 3.85 | 0.73 |
| 48-3 (T) | 4.29 | 3.30 | 0.99 | 2.88 | 1.41 |
| 17-1 | 4.38 | 3.23 | 1.15 | 2.85 | 1.53 |
| 17-1 + U | 4.70 | 3.98 | 0.72 | 3.78 | 0.92 |
| RUBELLA Valence | | | | | |
| 48-3 (T) | 3.33 | 3.18 | 0.15 | 2.81 | 0.52 |
| 48-3 + U | 3.43 | 3.06 | 0.37 | 3.05 | 0.38 |
| 48-3 (T) | 3.35 | 3.08 | 0.27 | 3.03 | 0.32 |
| 16-3 | 3.10 | 2.83 | 0.27 | 2.60 | 0.50 |
| 16-3 + U | 3.88 | 3.55 | 0.33 | 3.35 | 0.53 |
| 48-3 (T) | 3.28 | 2.87 | 0.41 | 2.74 | 0.54 |
| 17-1 | 2.93 | 2.43 | 0.50 | 2.35 | 0.58 |

TABLES A-continued

| STABILIZER | TITLES IN CCID 50/DOSE | | | | |
|---|---|---|---|---|---|
| | 7 days at 4° C. | 7 days at +37° C. | Loss (log) | 6 days at +45° C. | Loss (log) |
| 17-1 + U | 3.90 | 3.55 | 0.35 | 3.43 | 0.47 |

U = Urea 0.5% final

This stabilizing effect is essentially marked for the measles and mumps valences.

The rubella valence is comparatively stable with the three lyophilization excipients tested.

EXEMPLE 2

Stabilizing effect of several related compounds

Urea, thiourea and allylurea were tested with the same lyophilization excipient and for the three valences of the vaccine.

Acetamide, methylcarbamate and butylcarbamate were tested in the same way in relation to the mumps valence only, this being the most unstable.

The several tests were carried out for vaccines made in an excipient without inventive stabilizing compound (Control) and with an inventive stabilizing compound (investigated compounds). Titrations were carried out with these several compounds.

In this example all compounds are used at the same final concentration: 0.5%.

TABLES B

| STABILIZER | TITLES IN CCID 50/DOSE | | |
|---|---|---|---|
| | 7 days at +4° C. | 7 days at +37° C. | Loss (log) |
| MEASLES Valence: | | | |
| / | 4.05 | 3.52 | 0.53 |
| UREA | 4.11 | 3.75 | 0.36 |
| / | 4.21 | 3.59 | 0.62 |
| THIOUREA | 4.34 | 3.80 | 0.54 |
| / | 4.10 | 3.70 | 0.40 |
| ALLYLUREA | 4.43 | 3.90 | 0.53 |
| MUMPS Valence: | | | |
| / | 4.03 | 3.04 | 0.99 |
| UREA | 4.28 | 3.99 | 0.29 |
| / | 4.36 | 3.24 | 1.12 |
| THIOUREA | 4.64 | 3.98 | 0.66 |
| / | 3.90 | 3.05 | 0.85 |
| ALLYLUREA | 4.13 | 3.78 | 0.35 |
| | 4.45 | 3.20 | 1.25 |
| ACETAMIDE | 4.87 | 4.30 | 0.57 |
| | 4.45 | 3.20 | 1.25 |
| METHYLCARBAMATE | 4.70 | 4.20 | 0.50 |
| / | 4.48 | 3.70 | 0.78 |
| BUTYLCARBAMATE | 4.05 | 3.65 | 0.40 |
| RUBELLA Valence | | | |
| / | 3.33 | 3.18 | 0.15 |
| UREA | 3.43 | 3.06 | 0.36 |
| / | 3.21 | 2.83 | 0.37 |

TABLES B-continued

| STABILIZER | TITLES IN CCID 50/DOSE | | |
|---|---|---|---|
| | 7 days at +4° C. | 7 days at +37° C. | Loss (log) |
| THIOUREA | 3.20 | 3.03 | 0.17 |
| / | 3.48 | 3.08 | 0.40 |
| ALLYLUREA | 3.45 | 3.18 | 0.27 |

The stabilizing effects of these compounds are closely related and is mostly expressed for the mumps valence with the lyophilization excipient used.

In these examples the (not critical) detailed composition of the 48-3, 16-3 and 17-1 stabilizing excipients is the following:

48-3

(D+) Lactose, culture medium, human albumin, glutamic acid, monopotassium phosphate, bipotassium phosphate, potassium hydroxyde, arginine hydrochloride, cystine, histidine, isoleucine, leucine, lysine hydrochloride, methionine, phenylalanine, threonine, tryptophan, tyrosine, valine, alanine, asparagine, aspartic acid, glycine, proline, serine, (D-)sorbitol, (D-)mannitol, dextran 70 at relative concentrations of:

2-7 mg; 0.4-1.5 mg; 0.8-3 mg; 0.05-0.15 mg; 0.01-0.05; 0.05-0.2 mg; 0.008-0.05 mg; 2.4-6 mg; 0.02-0.06 mg; 0.018-0.05 mg; 0.05-0.2 mg; 0.05-0.2 mg; 0.08-0.20 mg; 0.01-0.05 mg; 0.04-0.10 mg; 0.05-0.15 mg; 0.008-0.02 mg; 0.03-0.10 mg; 0.05-0.12 mg; 0.015-0.05 mg; 0.02-0.08 mg; 0.02-0.08 mg; 0.015-0.05 mg; 0.02-0.06 mg; 0.02-0.05 mg; 5-15 mg; 2-8 mg; 1.5-4 mg; for one dose of final product.

16-3

Same formula as 48-3, but without mannitol.

17-1

Same formula as 48-3, but with differing proportions of some amino acids and sugars.

EXAMPLE 3

Effect of the stabilizing compound concentration on the stability of the triple vaccine This study was carried out with urea and allylurea on the three valences and in the presence of the lyophilization excipient of Example 2, for differing concentrations of inventive product varying between 0.125 and 2.0% final.

TABLES C

| | TITLES IN CCID 50/DOSE | | | | | | | | |
|---|---|---|---|---|---|---|---|---|---|
| | MEASLES | | | MUMPS | | | RUBELLA | | |
| Concentration % | 7 days at +4° C. | 7 days at +37° C. | Loss (log) | 7 days at +4° C. | 7 days at +37° C. | Loss (log) | 7 days at +4° C. | 7 days at +37° C. | Loss (log) |
| UREA: | | | | | | | | | |
| 0 | 3.30 | 2.75 | 0.55 | 3.80 | 2.83 | 0.97 | 3.50 | 3.43 | 0.07 |
| 0.125 | 3.60 | 3.23 | 0.37 | 4.25 | 3.45 | 0.80 | 3.73 | 3.33 | 0.40 |
| 0.25 | 3.70 | 3.18 | 0.52 | 4.20 | 3.60 | 0.60 | 3.80 | 3.20 | 0.60 |
| 0.50 | 3.40 | 3.15 | 0.25 | 4.13 | 3.88 | 0.25 | 3.68 | 3.33 | 0.35 |
| 1.0 | 3.60 | 3.20 | 0.40 | 4.20 | 3.65 | 0.55 | 3.35 | 3.33 | 0.02 |
| 2.0 | 3.35 | 3.05 | 0.30 | 4.10 | 3.90 | 0.20 | 3.35 | 3.33 | 0.02 |
| ALLYLUREA: | | | | | | | | | |
| 0 | 4.10 | 3.70 | 0.40 | 3.90 | 3.05 | 0.85 | 3.48 | 3.08 | 0.40 |
| 0.125 | 4.40 | 3.85 | 0.55 | 4.25 | 3.35 | 0.90 | 3.43 | 3.33 | 0.10 |
| 0.25 | 4.20 | 3.80 | 0.40 | 3.93 | 3.80 | 0.13 | 3.38 | 3.23 | 0.15 |

TABLES C-continued

| Concentration % | MEASLES | | | MUMPS | | | RUBELLA | | |
|---|---|---|---|---|---|---|---|---|---|
| | 7 days at +4° C. | 7 days at +37° C. | Loss (log) | 7 days at +4° C. | 7 days at +37° C. | Loss (log) | 7 days at +4° C. | 7 days at +37° C. | Loss (log) |
| 0.50 | 4.43 | 3.90 | 0.53 | 4.13 | 3.78 | 0.35 | 3.45 | 3.18 | 0.27 |
| 1.0 | 4.18 | 3.85 | 0.33 | 3.75 | 3.48 | 0.27 | 3.08 | 3.03 | 0.05 |
| 2.0 | 3.83 | ≦3.23 | ≧0.60 | 3.48 | 2.13 | 1.35 | 3.00 | 2.30 | 0.70 |

For urea the stability of the vaccine increases with the product concentration till 0.5%, after which the stability remains unchanged.

With allylurea the same increase in the vaccine's stability is obtained after which a decrease leading to a lower stability as compared with that of the control without allylurea is noted.

For this example the tests and titrations were put together for each product, for their performance, which enables one to compare the title levels at +4° C., +37° C., as well as the losses, obtained for the same product.

EXAMPLE 4

Effect of urea on measles, mumps, rubella vaccines which are lyophilized, rehydrated in the presence or absence of urea, then relyophilized The study was widened to include commercial vaccines. These vaccines, designated by A, B and C, do not all have the same mumps virus strain.

These vaccines were rehydrated with either water or a 0.5% urea solution, then relyophilized according to a standard cycle. The vaccines were treated under the same conditions, with the reference (applicant's vaccine, I.M.) being studied in the presence or absence of urea at the time of the first lyophilization and at the time of the second lyophilization.

The study was carried out on the most instable mumps valence only.

TABLE D

| VACCINE | | | +4° C. | 7 days at +37° C. | Loss | 6 days at +45° C. | Loss |
|---|---|---|---|---|---|---|---|
| I.M. | I | — | 4.50 | 3.70 | 0.80 | 3.03 | 1.47 |
| | | +U | 4.45 | 4.03 | 0.32 | 3.67 | 0.78 |
| | II | — | 4.00 | 3.55 | 0.45 | 2.98 | 1.02 |
| | | +U | 4.28 | 4.00 | 0.28 | 3.40 | 0.88 |
| A | II | — | 4.60 | 3.95 | 0.65 | 3.23 | 1.37 |
| | | +U | 4.38 | 4.13 | 0.25 | 3.55 | 0.83 |
| B | II | — | 3.80 | 3.38 | 0.42 | 3.18 | 0.62 |
| | | +U | 3.98 | 3.65 | 0.33 | 3.28 | 0.70 |
| C | II | — | 3.65 | 2.90 | 0.75 | 2.45 | 1.20 |
| | | +U | 3.50 | 3.58 | #0 | 2.80 | 0.70 |

I: normal vaccines (one lyophilization)
II: rehydrated and relyophilized vaccines in the presence or absence of urea
U: urea As appears from Table D urea increases the stability of mumps valence in I.M. vaccines, A and C. As for the B vaccine, the high stability noted after the second lyophilization does not enable to demonstrate the effect of urea.

We claim:

1. A process for stabilizing vaccines comprised of attenuated virus, said vaccines being in lyophilized form in the presence of at least one lyophilization excipient comprising adding to said vaccine before or after lyophilization a compound having the general formula:

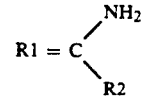

wherein R1 is an oxygen atom or a sulphur atom and R2 is a NH$_2$ group or a linear chain, unsaturated or not, selected from the group consisting of —O—C ..., —NH—C ..., and —C ..., in an amount sufficient to stabilize said vaccines against loss of activity.

2. Process according to claim 1, wherein the compound is urea.

3. Process according to claim 1, wherein the compound is thiourea.

4. Process according to claim 1, wherein the compound is allylurea.

5. Process according to claim 1, wherein the compound is acetamide.

6. Process according to claim 1, wherein the compound is methylcarbamate.

7. Process according to claim 1, wherein the compound is butylcarbamate.

8. Process according to claim 1, wherein the compound is used at a final concentration of about 0.5%.

9. Process according to claim 2, wherein urea is used at a final concentration of about 0.125-2%.

10. Lyophilized vaccine composition as obtained according to the process as defined in claim 1.

* * * * *